United States Patent [19]

Peterson

[11] Patent Number: 4,522,777
[45] Date of Patent: Jun. 11, 1985

[54] METHOD AND APPARATUS FOR MAKING CORRECTED CUSTOM FOOT MOLDS

[75] Inventor: William Peterson, Lake Placid, N.Y.

[73] Assignee: Peterson Laboratories, Lake Placid, N.Y.

[21] Appl. No.: 449,978

[22] Filed: Dec. 15, 1982

[51] Int. Cl.³ .................. B29C 17/00; B29D 31/00
[52] U.S. Cl. ........................... 264/223; 36/88; 128/595; 264/DIG. 30; 425/2
[58] Field of Search ............. 264/223, DIG. 30, 220, 264/222; 12/142 N, 38, 21, 146 M; 425/2, 129 S; 36/93, 88; 128/595, 80 DB

[56] References Cited

U.S. PATENT DOCUMENTS

| | | | |
|---|---|---|---|
| 249,438 | 11/1881 | Winslow | 425/119 |
| 964,119 | 7/1910 | Norton | 425/2 |
| 1,044,170 | 11/1912 | Guilford | 425/2 |
| 1,044,171 | 11/1912 | Guilford | 264/223 |
| 1,464,501 | 8/1923 | Engel | 12/18.3 |
| 1,730,466 | 10/1929 | Mallot | 128/581 |
| 1,856,394 | 5/1932 | Lettermann | 264/DIG. 30 |
| 2,330,398 | 9/1943 | Vass | 128/619 |
| 2,440,508 | 4/1948 | Gould | 264/223 |
| 2,499,324 | 2/1950 | Mead | 264/220 |
| 2,565,758 | 8/1951 | Covino | 264/223 |
| 2,742,657 | 4/1956 | Sloane | 12/146 R |
| 2,742,717 | 4/1956 | Murray | 128/595 |
| 2,856,633 | 10/1958 | Murray | 264/223 |
| 2,891,285 | 6/1959 | Kaplan | 264/223 |
| 2,955,326 | 10/1960 | Murray | 264/138 |
| 2,973,529 | 3/1961 | Silverman | 12/142 H |
| 3,310,885 | 3/1967 | Alderson | 425/2 |
| 3,320,347 | 5/1967 | Greenawalt | 264/223 |
| 3,380,123 | 4/1968 | Schmidt | 249/151 |
| 3,398,221 | 8/1968 | Sherman et al. | 264/223 |
| 3,444,586 | 5/1969 | Dubner | 425/129 |
| 3,458,898 | 8/1969 | Casparis | 425/2 |
| 3,541,646 | 11/1970 | Baudou | 425/119 |
| 3,655,306 | 4/1972 | Ross | 425/521 |
| 3,662,057 | 5/1972 | Webster et al. | 264/DIG. 30 |
| 3,684,417 | 8/1972 | Baudou | 425/119 |
| 4,139,337 | 2/1979 | David | 425/2 |

OTHER PUBLICATIONS

Brochure entitled "Conform'able SIDAS" printed by SIDAS, Grenoble, France.

Primary Examiner—Jan Silbaugh
Assistant Examiner—Hubert C. Lorin
Attorney, Agent, or Firm—Richard M. Goldberg

[57] ABSTRACT

Apparatus for producing a corrected mold for a foot having a rear portion and a forefoot portion, includes a resilient cushion which relatively immobilizes the forefoot portion with respect to the rear portion thereof when the foot is supporting its respective portion of full body weight, the resilient cushion having a rear section with a first thickness and a front section with a second, smaller thickness for supporting the foot, wherein the position of the rear portion of the foot on the resilient cushion is adjusted so that the resilient cushion adopts a corrected contour of the foot; a stabilizer which aligns and stabilizes the knee corresponding to the foot to a predetermined alignment with respect to the forefoot portion of the adjusted foot when the foot is positioned on the resilient cushion; and a molding material positioned between the foot and the resilient cushion for producing the corrected mold once the foot has been so adjusted and the knee has been so aligned.

12 Claims, 12 Drawing Figures

METHOD AND APPARATUS FOR MAKING CORRECTED CUSTOM FOOT MOLDS

BACKGROUND OF THE INVENTION

This invention relates to novel methods and apparatus for making corrected custom molds of the human feet, from which orthopedic devices, or orthoses, for the foot can be fabricated. Such devices are now commonly referred to as "foot orthotics".

Knowledge of the mechanics of the human foot will help in understanding this invention. Made up of a complex array of twenty-six bones, the human foot performs two main functions, support and locomotion. Ideally, the foot functions as a tripod, supporting the body's weight on the heel and across the metatarsal arch. The foot is capable of a wide range of movement, including up and down, in and out, and side to side. Under stressed conditions, one of the most important of these movements is the side to side rotation of the foot, either to the outside ("supination") or to the inside ("pronation"). This rotation increases or decreases the height of the foot's arches, and if excessive, can put the foot in a weakened, unbalanced, condition. The foot is said to be in a "neutral" position when it is neither pronated nor supinated, i.e., when the heel bone is vertical and is directly in line with the talus bone above it. The neutral position provides good skeletal support for the body's weight.

However, it is known that knee position in relation to foot position is also an important factor in providing the maximum support for the body, particularly when the foot is in a full weight-bearing condition. As the foot pronates, the knee will tend to rotate to the inside, and conversely, as the foot supinates, the knee will tend to rotate to the outside. For the best balance and least stress, the knee should be aligned over the weight-bearing center of the foot. However, due to differences in individual structure, the knee may well be somewhat inside or outside its ideal position when the foot itself is placed in "neutral" (as defined above). Furthermore, putting the knee in its ideal position may leave the foot too far from neutral. In order to achieve the maximum skeletal support, one must balance both the position of the foot and the position of the knee. Failure to do so can place unnecessary stress on the foot, the knee and the rest of the body.

While so far we have only discussed the foot at rest, it is well known that activities which involve movement of the body, including walking, running, skiing, and skating, place very large stresses on the bones and joints of the leg and the foot. These stresses are large when the bones and joints of the foot are not in the proper position, and are maximized when the knee is additionally out of its proper alignment.

In the past, improper foot structure and position have sometimes been treated in part through custom-molded foot orthotics which fit into the shoes and which support the foot, or parts of the foot, in a "corrected" position. This corrective function of a foot orthotic distinguishes it from a mass-produced foot pad or other shoe insert designed strictly for comfort. Up to now, however, custom foot orthotics have been molded by archaic, complicated, time-consuming and expensive methods. For example, foot orthotics have often been molded (1) from actual foot measurements, (2) from a mold made of bandages coated with wet plaster which are wrapped around the foot until hard, and then cut off, (3) from a mold made by holding the foot motionless in wet plaster until hard and then cutting the mold open, and (4) from a directly molded heat-softening substance such as plastic. Therapeutic results with foot orthotics molded by these methods have tended to be inconsistent. First, by previous methods, it has usually been impossible to obtain a fully corrected mold of the foot, and thus the final device must be posted, or propped up with use of wedges on one side or the other, either in the forefoot, rear foot, or both, to achieve the desired result. Second, molding systems and/or techniques have rarely considered body structure above the foot, specifically the position of the knee in relationship to the foot. Even when the relationship between the position of the knee and the foot has been considered, no means of accurately and consistently measuring or determining the proper alignment between the position of the knee and the foot has existed, and no method or technique for molding a foot orthotic has been known which holds the foot and knee in that proper alignment during the molding operation. In addition, it now appears that foot orthotics for different activities, e.g. walking vs. running vs. skiing, may demand slightly differing positions for the bones of the foot and slightly differing adjustment between the knee and the foot. Such minute and subtle differences in position and alignment have been impossible to achieve accurately in foot orthotics molded by past methods and techniques.

OBJECTS AND SUMMARY OF THE INVENTION

It has now been discovered that corrected molds, from which comfortable and extremely functional foot orthotics can be fabricated, may be repeatably and inexpensively prepared by a novel molding technique and apparatus which is easy-to-use and remarkably sensitive to minute changes in foot and knee position.

Thus, it is a principal object of the present invention to provide a novel method for making corrected custom molds of the feet from which foot orthotics can be easily fabricated.

It is also an object of this invention to provide a novel method for making corrected custom molds of the feet, which includes an apparatus for quickly, accurately and repeatably placing each foot and its associated knee in the correct, balanced position, and allows each foot to be molded in that position.

It is still a further object of this invention to provide a novel apparatus for making corrected custom molds of the feet, which provides an inexpensive but uniform and highly reliable mold every time.

It is still even a further object of this invention to provide as the novel molding apparatus a platform for the patient to stand on which comprises a specially-contoured resilient molding cushion and which further comprises a unique adjustable knee stabilizer apparatus.

It is still yet another object of this invention to provide such an adjustable knee stabilizer apparatus which mechanically measures proper knee alignment and then effectively maintains that alignment during the actual molding operation.

It is even yet another object of this invention to provide a novel apparatus for making corrected custom molds of the feet, which mechanically allows the making of different molds for the same patient which differ from each other only in terms of minute differences in foot and knee alignment, and which may then be fabricated into therapeutically-different and functionally valuable foot orthotics.

The present invention, as well as further objects and advantages thereof, will be more fully understood from the following description of a preferred embodiment, when read with reference to the accompanying drawings.

DESCRIPTION OF A PREFERRED EMBODIMENT

Figure 1:
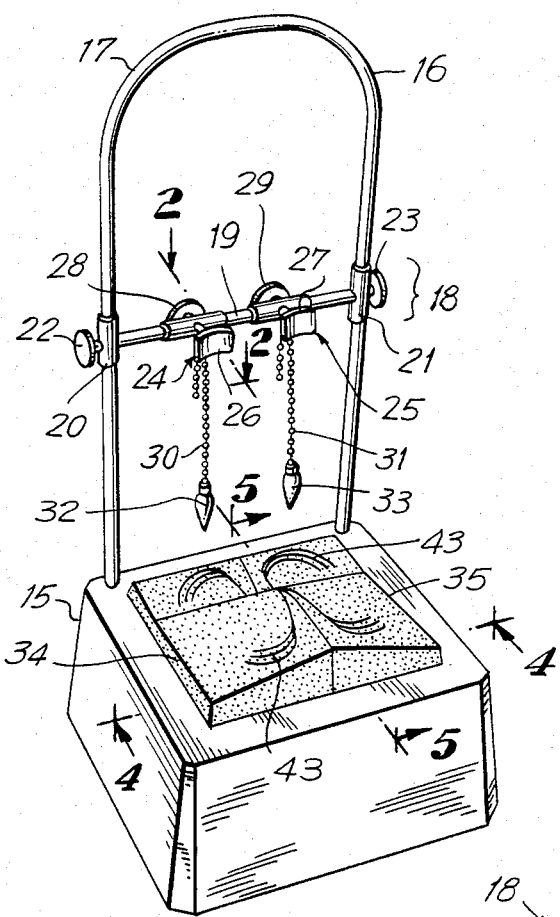
FIG. 1 is a perspective view of molding apparatus in accordance with an illustrative embodiment of this invention.

Referring to the drawings, FIG. 1 shows apparatus having a molding platform including a base 15, which is preferably at a height where the molding technician can easily examine the feet of the patient. Attached to the front of the base is an adjustable handrail 16, which rises from the front of the platform as an upside down U-shaped piece of tubular steel 17 of sufficient height so that the patient may comfortably hold on to it while he or she is standing on the base. In practice the handrail 16 can be of any configuration or material as long as it provides the necessary stability for the customer.

Figure 2:
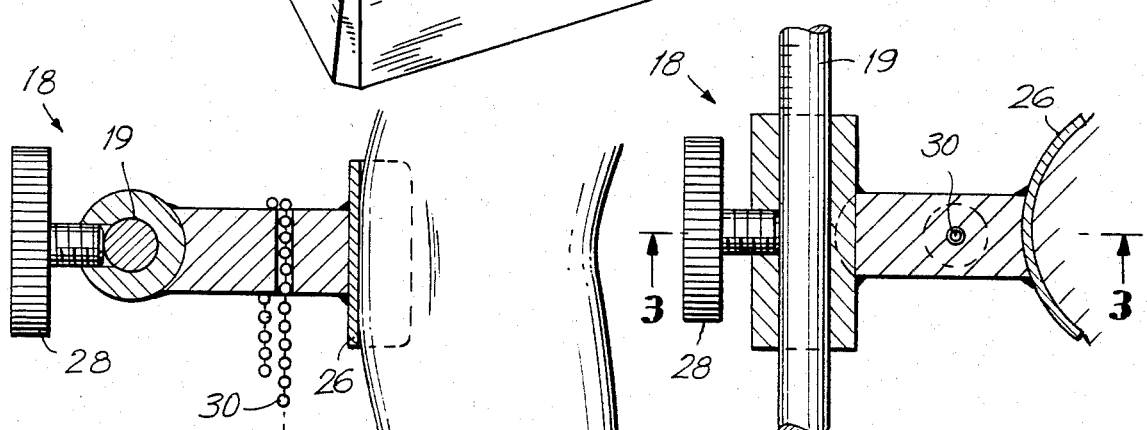
FIG. 2 is a top plan view of the novel adjustable knee stabilizer portion of the apparatus shown in FIG. 1.
Figure 3:
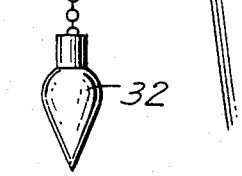
FIG. 3 is a cross-sectional view of the knee stabilizer apparatus taken along the line 3—3 in FIG. 2.

The platform also includes an adjustable knee stabilizer apparatus, seen generally as 18. As shown in more detail in FIGS. 2 and 3, the knee stabilizer apparatus 18, preferably attached to the handrail, is a cross-bar of tubular steel 19 attached on both ends to the raised up side portions of the handrail by sliding members 20 and 21. The cross bar 19 is adjustable in an up and down direction by means of lock wheels 22 and 23 connected to the sliding members 20 and 21. Two knee cups 24 and 25 are attached to the cross bar 19. Preferably the knee cups are made from curved pieces of steel or plastic 26 and 27 attached to locking mechanisms 28 and 29 which permit each cup to slide across the cross bar 19 into any desired position. Suspended from knee cups 24 and 25 are plumb lines including chains 30 and 31 bearing pointed weights 32 and 33. The weights 32 and 33 are used to line up the knees with the feet before molding. However, any configuration for the knee cups is suitable as long as it permits the knee to be positioned and then held in place during the molding operation.

Figure 4:
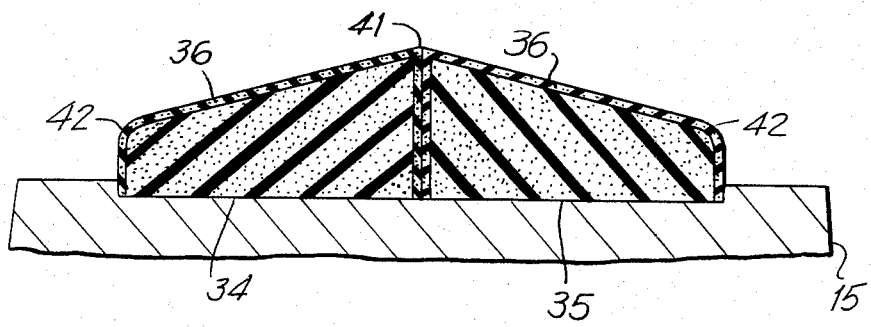
FIG. 4 is a cross-sectional view of the novel molding cushion portion of the apparatus taken along the line 4—4 in FIG. 1.
Figure 5:
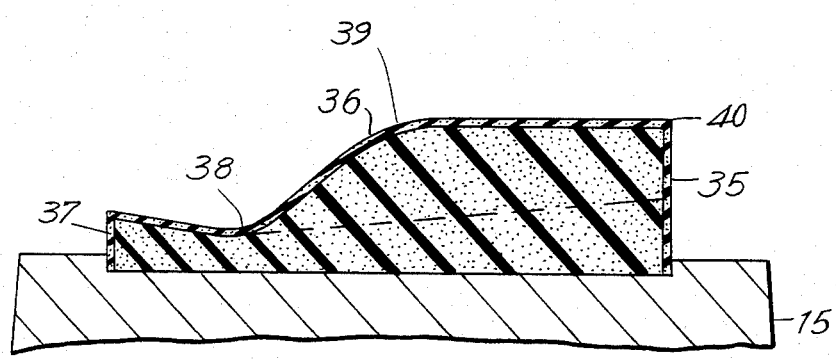
FIG. 5 is a cross-sectional view of the novel molding cushion taken along the line 5—5 in FIG. 1.

Mounted on top of the base 15 are two specially-contoured cushions 34 and 35. With particular reference to FIGS. 4 and 5, each cushion is the mirror image of the other and is constructed of elastic material, preferably polyurethane foam of firm density chosen for its outstanding resilience. Although in the preferred embodiment, it is advantageous to use two separate cushions, such as cushions 34 and 35, it is not absolutely necessary to use two cushions, and thus the whole cushion may be made from one piece of resilient material. However, in the preferred embodiment, two cushions are used and each is covered with a one-eighth inch layer of neoprene foam 36. Although not shown, each cushion may then be covered with a thin layer of four-way stretch nylon which is helpful in preventing the molding material from sticking to the cushions and adds to their overall durability and appearance. Advantageously, each cushion may be covered with one material which provides both the layer of foam and the layer of four-way stretch nylon. Such a material is marketed under the trade name "Spenco" or "Lynco".

Figure 7:
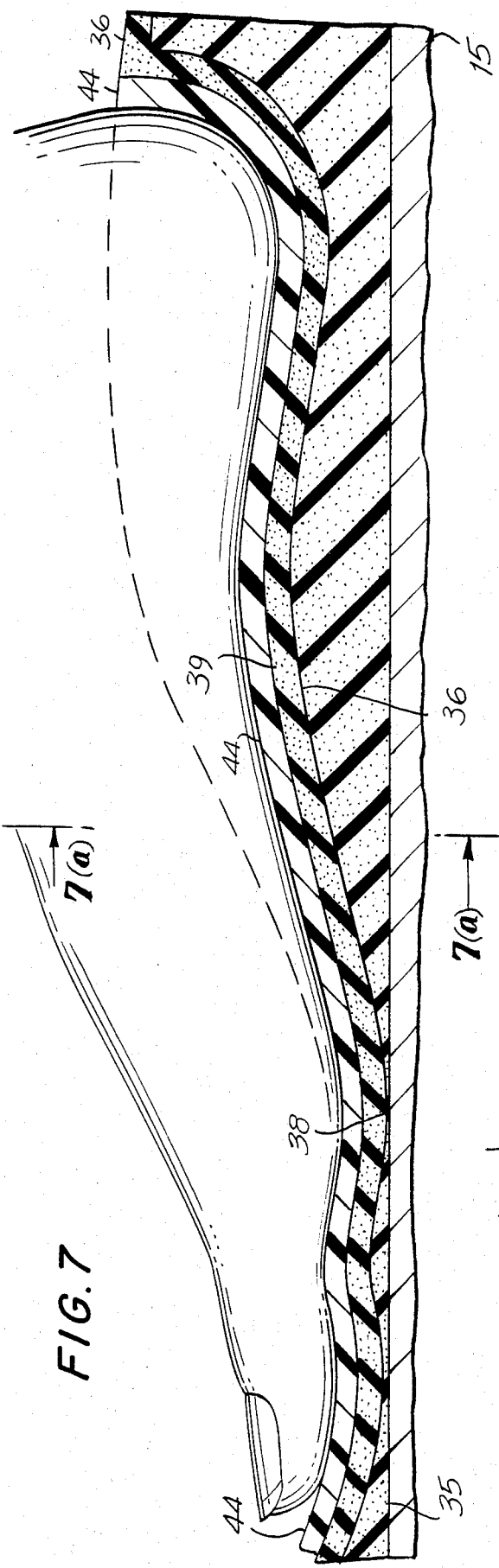
FIG. 7 is an enlarged fragmentary cross-sectional view taken along the line 7—7 in FIG. 6.

In the preferred embodiment, the cushions 34 and 35 are specially-contoured to promote optimal bone alignment in each foot. More particularly, and with reference to FIG. 5, each of the cushions 34 and 35 is approximately one and one-half inches high at front edge 37, dropping down to about 1 inch in the metatarsal or toe region 38 and then rising steadily from that point to a height of about four inches at the approximate center of the arch at 39. From that point to the rear 40, the cushion drops down slightly. As shown more clearly in FIG. 7, when the patient puts his or her foot onto the cushion 34, the ball of the foot is brought down to the flat surface at 38, compressing the cushion to the point where the forefoot is rendered relatively immobile. The arch and rear portion of the foot, however, compress the contoured cushion at 39 only part way down, permitting the arch and rear portion of the foot to be more mobile than the forefoot. In essence, the arch and rear portion of the foot "float" in the resilient material of the cushion. This floating of the arch and rear portions of the foot in the cushion, combined with stabilization of the forefoot, allows for proper alignment of the joints and bones of the foot without the distortion which can be caused by full weight-bearing throughout the whole length of the foot, and additionally increases the potential for total correction of overall foot structure. Furthermore, the slight upward slope of the cushion in the front tends to stretch out the toes which in turn tightens the muscles and tendons of the foot and makes it more stable for molding. In practice, however, any configuration or construction of the cushion is acceptable if it permits the arch and rear parts of the foot to be elevated in relation to the forefoot and permits the ball of the foot to compress the cushion to a greater extent than the arch and rear portion of the foot, thus causing the latter to "float" in the material of the cushion. Because of this "floating" action due to the relatively mobile arch and rear portion of the foot in relation to the forefoot the position of the foot, and, in particular, of the rear portion thereof, is adjusted so that the cushion adopts a corrected contour of the foot.

It can also be seen in FIG. 4 that each of the cushions 34 and 35 in the preferred embodiment of this invention is also cut away at an angle sideways so that each cushion slopes down from the inside 41 to the outside 42. This slope of the cushion is designed to help in correcting the pronated foot by compensating for internal distortion in the structure of the bones and joints of the foot. Although an angle of seventeen degrees has been found to work well in the practice of this invention and is used in the preferred embodiment, the exact degree of angle may vary anywhere between about 0° and 20°.

Figure 7A:
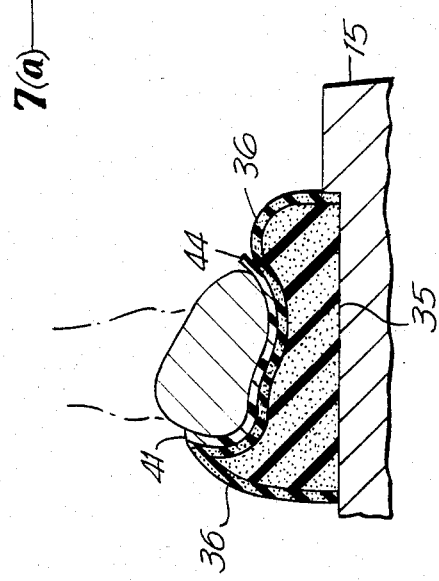
FIG. 7(a) is an enlarged fragmentary cross-sectional view taken along the line 7(a)—7(a) in FIG. 7.

When two molding cushions are used, as in the preferred embodiment, the inside edge 41 of each cushion may be made extremely sharp and distinct. When the patient stands on such a cushion, as shown in FIG. 7(a), the sharp inside edge of the cushion wraps in forcefully around the inside edge of the foot, adding extra support to the arch and holding the material being molded tightly to the foot. One expediency to make the inside edge 41 sharp and distinct is to make the foam covering 36 for the top, front, back and outside edge of the cushion from one continuous piece of material. The inside surface is then covered with a totally separate piece of foam which thus creates a visible, sharp and distinct seam along the border of the top and inside surface of the cushion at 41.

Figure 6:
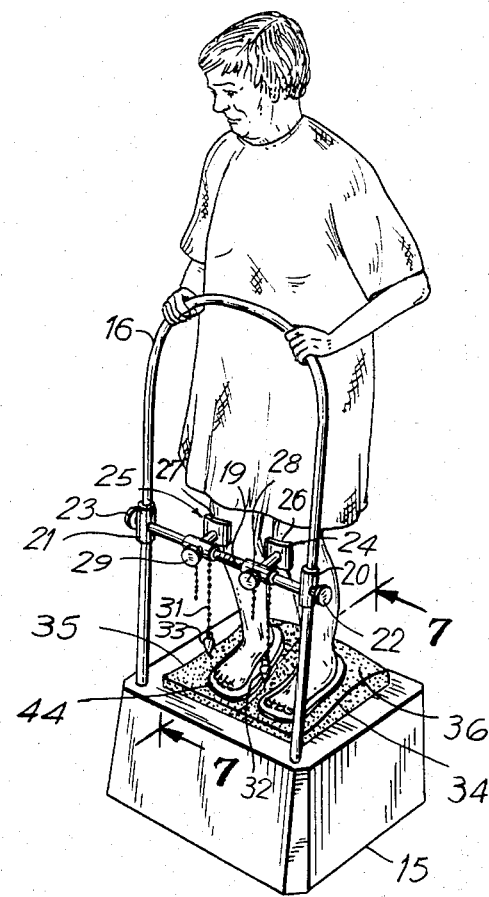
FIG. 6 is a perspective view similar to FIG. 1 but showing the apparatus in use.

With reference now to FIG. 6, the patient stands barefoot on the molding apparatus of FIG. 1 with his feet in the proper position on the molding cushions. Attaining the proper position on the cushion may be aided by having drawn or printed on the cushion an outline of the foot in the correct position, as is shown in FIG. 1 at 43. Making sure that the patient's body position is correct, i.e., knees in the knee cups and back straight (which will automatically take stress off the arches and the rear portions of the feet), the technician adjusts the knee cups 24 and 25 using the pointed weights 32 and 33 so that each knee is positioned over the weight-bearing center of each foot, which in the practice of this invention, may initially be taken as over the second toe of the foot. The technician then checks the structure of each foot by methods well-known in the art to see if the foot is pronated, supinated or in neutral. The floating and tilting action of the cushions, combined with realignment of the knees, will generally result in the correction of most structural problems.

At this point, additional adjustments can be made based on (a) an examination of the patient, (b) knowledge of the patient's specific problems, and (c) knowledge of the activity for which the ultimate foot othotic will be used. For example, and only by way of illustration, if, after the technician has adjusted the patient's knees according to the method above, it appears that one or both of the patient's feet are still excessively pronated, the knee cup(s) may be moved out slightly, which will compensate for and correct excessive pronation. Conversely, if one or both feet remain excessively supinated, the knee cup(s) may be moved slightly to the inside. In either case, foot correction is achieved through accurate consideration of knee position thereby avoiding past problems which have resulted in general from a consideration only of foot structure.

Once the technician determines that the patient is in the correct position, the feet can be molded. The molding sheet 44 may consist of a piece of thermoplastic material larger in length and width than the foot to be molded, as shown under the foot of the patient in FIG. 6. Of course, if the finished foot orthotic is only desired to support the arch and rear portion of the foot, the initial molding sheet does not have to extend under the toes, but can be, for example, only three-fourths the length of the foot.

Any material which can be made sufficiently pliable to make a mold and can then be hardened to retain its molded shape may be used. A preferred material is one which becomes pliable on heating and then hardens again on cooling, as long as it is remembered when using such a material either that the molding temperature must be low enough to avoid burning the foot of the patient, or that an insulating material must be placed between the patient's foot and the heated material.

One such preferred material is a sheet of thermo-plastic such as 44. Sheet 44 may be prepared for molding by placing it in an oven at a sufficient temperature and for a sufficient time to soften the sheet. One such preferred molding sheet is made from two separate layers of plastic glued together to make one sheet. The top layer may consist of about one-eighth inch thick of a closed-celled polyethylene foam, while the bottom layer may consist of about a one-eighth inch thick sheet of low-density polyethylene plastic. This two-layer sheet will reach a sufficiently soft state for molding when the low-density polyethylene has reached about 225°–250° F. The foam layer on top will not be as hot as the polytheylene sheet below it and will insulate the patient's foot from the hotter layer.

When the sheet 44, regardless of the type chosen, has sufficiently softened in the oven, the patient lifts one foot off the platform, the now-pliable sheet is put in place under the foot, and the technician places the patient's foot back onto the sheet. The technician then rechecks the foot and knee for correct positioning and alignment. In most cases, the patient should have his or her weight equally balanced between both feet. After two to three minutes, the molded sheet should be sufficiently cooled so that it is hard. The result is a direct negative mold of the patient's foot in a corrected position (a so-called "corrected mold.") The molding technique is then repeated on the other foot.

Figure 8:
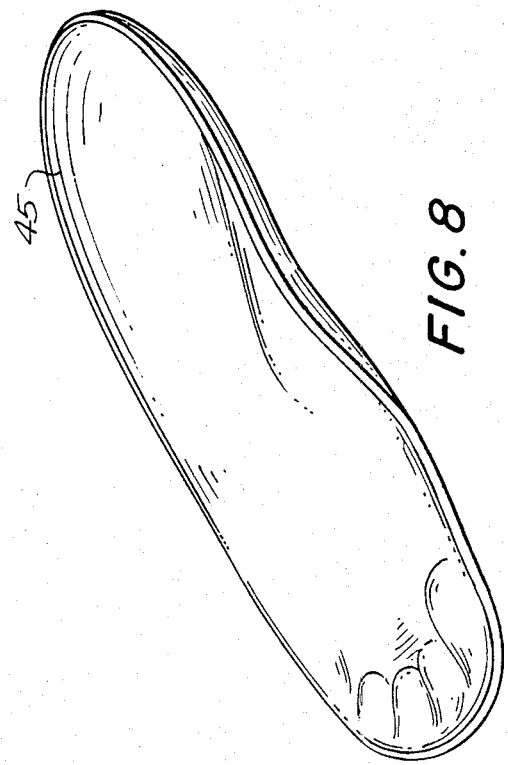
FIG. 8 is a perspective view of a foot orthotic core after molding on the apparatus of FIG. 6 and after trimming excess material.

Once a sheet 44 has been molded for each foot, a finished foot orthotic can be prepared by actually using the molded sheet 44 as the core of the orthotic, or by using the molded sheet to make a positive plaster cast from which a foot orthotic may then be constructed. In the first case, excess material may first be cut off around the molded sheet, resulting in the molded core 45 shown in FIG. 8. If support of a full-length core is not necessary, the molded sheet can be trimmed back to three-fourths of its length as shown, for example, in FIGS. 10 and 11 (or, as stated above, a three-fourths length molding sheet may be initially used). The core 45 is then checked by methods well-known in the art for correct alignment of the foot, proper molding and proper lamination of materials. However, if correct alignment was initially obtained using the apparatus of this invention, no further changes will be necessary.

Using additional techniques well-known in the art, and depending on the requirements for the finished device, foam supports of varying density may be glued to the bottom of the core using any adhesive suitable for plastic materials. In some cases, different density foams may be added to the bottom to give the foot orthotic any range of flexibility and cushioning desired. The combination of the core and the foam is then ground to the desired degree of flatness on the bottom and contour on the sides. Other foam, cushioning, or cloth materials may also be added to the top and the bottom of the orthotic for additional comfort, wearability and appearance.

Figure 9:
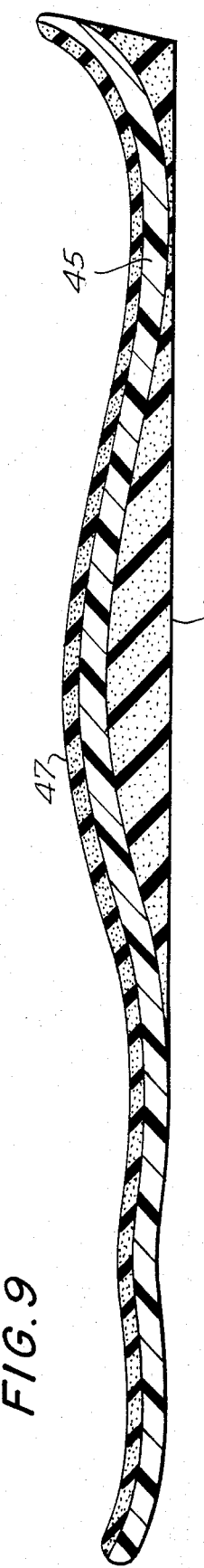
FIG. 9 is a vertical cross-sectional view of a full-length foot orthotic with a full-length core directly molded by the method of this invention.

FIG. 9 shows a finished full-length corrective foot orthotic comprised of a full-length core 45 directly molded by the method of this invention, and which provides support and correction through the entire length of the foot. Foam 46 is added to the bottom for additional support and a cushioning material 47 may be to the top to complete the device. A foot orthotic as shown in FIG. 9 may be suitable for activities where forefoot flex is not desirable, e.g, snow skiing.

Figure 10:
FIG. 10 is a vertical cross-sectional view of a full-length orthotic with a three-fourths length core directly molded by the method of this invention.

FIG. 10 shows a finished full-length corrective foot orthotic comprised of a three-fourths length core directly molded by the method of this invention, and which provides support and correction to the arch and the rear part of the foot while allowing flexibility in the forefoot. A full-length layer of cushioning material 47 has been added to the top and an additional layer of durable material 48 has been added to the bottom. A foot orthotic as shown in FIG. 10 may be suitable for activities where forefoot flex is necessary or desired, e.g., running.

Figure 11:
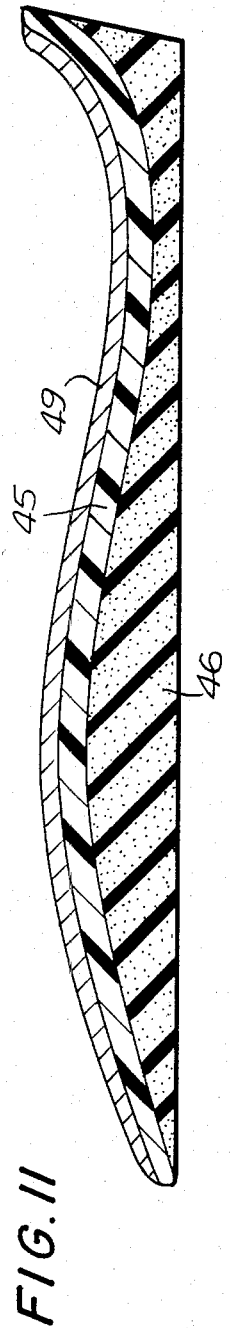
FIG. 11 is a vertical cross-sectional view of a three-fourths length foot orthotic with a three-fourths length core directly molded by the method of this invention.

FIG. 11 shows a finished three-fourths length corrective foot orthotic comprised of a three-fourths length core directly molded by the method of this invention. A cosmetic finishing material 49, such as leather, has been added to the top. A foot orthotic as shown in FIG. 11 may be suitable for everyday wear, as in street shoes.

Although the invention has been described and illustrated as being particularly useful for constructing corrective foot orthotics using as a core the actual corrected mold made using the methods and apparatus of this invention, the methods and apparatus may also be advantageously employed to make a mold of the foot which can then be used, in accordance with techniques well-known in the art, to make a positive plaster cast from which the foot orthotic can then be obtained by remolding. As an illustration, the molded sheet 44 obtained by using the molding apparatus of this invention can be used to create a plaster mold of the contours of the foot. From this mold, any type of foot orthotic from any type of material may be generated. Various other uses for the methods and apparatus will suggest themselves to those skilled in the art upon reading the foregoing disclosure.

The terms and expressions which have been employed are used as terms of description and not of limitation, and there is no intention in the use of such terms and expressions of excluding any equivalents of the features shown and described, or portions thereof, it being recognized that various modifications are possible within the scope of the invention claimed.

What is claimed is:

1. In apparatus for producing a corrected mold for a foot having a rear portion and a forefoot portion with a ball portion, said apparatus comprising:
resilient cushion means for substantially immobilizing the ball portion and providing a floating action for the rear portion thereof when said foot is supporting its respective portion of full body weight, said resilient cushion means having a rear section with a first thickness for supporting said rear portion and a front section with a second, smaller thickness for supporting said forefoot portion, said rear section being deformable throughout the entire first thickness thereof to provide the floating action, the second thickness being sufficiently small such that said ball portion completely compresses said front section at the respective position of the ball portion to provide said substantial immobilization, wherein the position of the rear portion of the foot on the resilient cushion means is adjusted so that said resilient cushion means adopts a corrected contour of the foot; and
molding means positioned between said foot and said resilient cushion means for producing said corrected mold once said foot has been so adjusted.

2. Apparatus according to claim 1, in which said molding means is comprised of a sheet of plastic which softens on heating and hardens on cooling.

3. Apparatus according to claim 1, in which said resilient cushion means includes an inner portion and at least one outer portion, said inner portion being at a higher level then said at least one outer portion.

4. Apparatus according to claim 1, in which said resilient cushion means includes an inner portion and includes an upper support surface which is inclined downwardly from said inner portion.

5. Apparatus according to claim 4, in which said upper support surface of said resilient cushion means is inclined downwardly from said inner portion with an angle which is not greater than 20°.

6. Apparatus according to claim 1, in which said resilient cushion means includes first and second sections, each section having a raised end portion, said raised end portions of said first and second sections being adjacent to each other, and each of said first and second sections being adapted to support a foot.

7. Apparatus according to claim 1, in which said resilient cushion means includes a front edge, and said front section of said resilient cushion means includes an upper surface which is inclined upwardly towards said front edge when said cushion means is not depressed.

8. Apparatus according to claim 1, in which said resilient cushion means includes an upper surface which is inclined upwardly from said front section to said rear section.

9. A method for producing a corrected mold for a foot having a rear portion and a forefoot portion with a ball portion, said method comprising the steps of:
substantially immobilizing the ball portion of said foot when said foot is supporting its respective portion of full body weight by supporting the foot on resilient cushion means having a rear section with a first thickness for supporting said rear portion and a front section with a second, smaller thickness for supporting said forefoot portion, the second thickness being sufficiently small such that said ball portion completely compresses said front section at the respective position of the ball portion to provide said substantial immobilization;
supporting the rear portion of the foot on said rear section in a floating manner with said rear section being deformable throughout the entire first thickness thereof to provide the support in said floating manner;
adjusting the position of the rear portion of the foot on said resilient cushion means so that said resilient cushion means adopts a corrected contour of the foot; and
making a mold of said adjusted foot from molding means positioned between said foot and said resilient cushion means.

10. The method according to claim 9, in which said molding means is comprised of a sheet of plastic which softens on heating and hardens on cooling.

11. The method according to claim 9, in which said resilient cushion means includes an inner portion and an upper support surface which is inclined downwardly from said inner portion with an angle which is not greater than 20°.

12. In apparatus for producing a corrected mold for a foot having a rear portion and a forefoot portion, said apparatus comprising:

resilient cushion means for relatively immobilizing the forefoot portion with respect to the rear portion thereof when said foot is supporting its respective portion of full body weight, said resilient cushion means having a rear section wth a first thickness for supporting said rear portion and a front section with a second, smaller thickness for supporting said forefoot portion, said rear section being deformable throughout the entire first thickness thereof, and said resilient cushion means including a front edge, and said front section, in order to stretch out the toes and to tighten the muscles of the foot to the extent that it makes the foot more stable, includes an upper surface which is inclined upwardly towards said front edge when said cushion means is in an undepressed state, wherein the position of the rear portion of the foot on the resilient cushion means is adjusted so that said resilient cushion means adopts a corrected contour of the foot; and molding means positioned between said foot and said resilient cushion means for producing said corrected mold once said foot has been so adjusted.

* * * * *